United States Patent [19]

Chiang

[11] Patent Number: 4,919,133

[45] Date of Patent: Apr. 24, 1990

[54] CATHETER APPARATUS EMPLOYING SHAPE MEMORY ALLOY STRUCTURES

[76] Inventor: Tien-Hon Chiang, 63 Finisterra, Irvine, Calif. 92714

[21] Appl. No.: 233,417

[22] Filed: Aug. 18, 1988

[51] Int. Cl.⁵ .............................................. A61B 17/32
[52] U.S. Cl. .................................... 606/159; 604/281; 606/170; 606/180
[58] Field of Search ....................... 604/281, 220, 264; 128/348.1, 305

[56] References Cited

U.S. PATENT DOCUMENTS

| | | | |
|---|---|---|---|
| 4,170,990 | 10/1979 | Baumgart et al. | 128/924 N |
| 4,461,305 | 7/1984 | Cibley | 128/754 |
| 4,655,171 | 4/1987 | Wallsten | 604/281 |
| 4,665,906 | 5/1987 | Jervis | 128/924 N |
| 4,685,458 | 8/1987 | Leckrone | 128/305 |
| 4,781,186 | 11/1988 | Simpson et al. | 128/305 |

Primary Examiner—Stephen C. Pellegrino
Attorney, Agent, or Firm—Leonard Tachner

[57] ABSTRACT

An improved catheter of the type used for mechanically removing arterial plaque employs shape memory alloy structures in the form of an integral portion of the catheter housing for compression against the artery wall and storage of pieces of plaque and at least one actuatable door for selectively opening and closing a window in the housing. The shape memory alloy material is heated by a remotely located current source connected to the catheter by conductors for selective activation of the alloy for a reversible change in shape such as expansion and elongation.

14 Claims, 7 Drawing Sheets

CATHETER APPARATUS EMPLOYING SHAPE MEMORY ALLOY STRUCTURES

BACKGROUND OF THE INVENTION

1. Field of the Invention

The present invention relates generally to catheters and more specifically, to an improved catheter which incorporates shape memory alloy structures comprising an expandable catheter housing wall and a shutter mechanism for enhancing the operation of the catheter.

2. PRIOR ART

Angioplasty, a cardiological therapeutic procedure for removing plaque deposits in blocked arteries has become increasingly popular among cardiovascular surgeons as a substitute for bypass or vascular graft surgery among some patients. Currently, balloon and laser angioplasty are the most frequently used clinical procedures. The balloon simply pushes the clotted vessel locally to enlarge the narrowed artery. The laser method literally evaporates the deposited plaque. However, neither of these procedures is effective in cases in which the plaque has been calcified. Recently a new type of catheter called the "Simpson Atherocath" has been clinically tested and has shown promising results. This new catheter utilizes a rotational cutter which removes atheroma through a longitudinal cut-out on a cylindrical housing located at the distal end of a catheter. One major disadvantage of the Simpson Atherocath is that the catheter has to be removed from the patient's blood vessel several times during the catheterization process to empty the plaque collection chamber when it is full. Such repeated removal and reinsertion of the catheter into the patient's blood vessel, causes a high level of discomfort to the patient who has to lie motionless for several hours on an operating table. In addition, it also increases the substantial risk of developing other complications during the angioplasty procedure. A detailed description of the atherocatheter and its components is provided in U.S. Pat. Nos. 4,669,469; 4,461,305; 4,616,648; and 4,616,652.

Shape memory alloy material has been known for some time. By way of example, in an article entitled "Shape Memory Alloys" written by L. McDonald Schetky and appearing in Scientific American, November 1979 beginning at page 74, the author thoroughly explains the mechanical properties of these alloys and indicates that they first came to worldwide attention in 1962. As further explained in that article the phenomenon of shaped memory alloys is dependent upon the characteristic of certain materials to possess a martensite crystal structure derived from a parent crystal phase when treated by a certain combination of stress and temperature processing. This martensitic crystal phase can then be transformed back into its parent crystal phase thermoelastically by elevating the temperature of the material. In addition, for certain "two-way" shape memory alloys, this phase transformation can be reversed by lowering the temperature of the material. As a result of these phase transformations, the material can be induced to change its shape in a carefully controlled and reversible manner by simply controlling the temperature of the material to induce the aforementioned phase transformations. The article by Schetky illustrates a particular exploitation of this phenomenon for automatically deploying an antenna for a spacecraft. An updated description of the "Shape Memory Effect Alloys" can also be found in the Encyclopedia of Materials Science and Engineering, Volume 6, pages 4365–4374 MIT Press, 1986.

Numerous patents have been issued with regard to the use of shape memory alloy materials in the medical device industry. by way of example, U.S. Pat. Nos. 4,411,655 and 4,665,906; Japanese Pat. Nos. 59/067968; 61/193670 and 87/020827; and European Pat. Nos. 145,166 and 244,818 disclose the use of shape memory alloy materials in catheter applications. However, the use of the multi-purpose structure described herein for catheter applications has not been disclosed previously in any prior art known to the applicant.

SUMMARY OF THE INVENTION

The present invention comprises an improved catheter design which utilizes a shape memory alloy structure as part of the wall of the housing structure of a Simpson Atherocath catheter or other similar types of catheters and may also use a shape memory alloy material as at least one actuator for a thin shutter door to open and close a radially disposed opening in such a catheter. The wall structure portion of the present invention employing shape memory alloy comprises a combination of shape memory alloy and elastomer in a composite membrane structure fabricated in such a way that it can expand as desired like a balloon, but without utilizing gas pressurization for the purpose of structural inflation. As a result, the expanded shape memory alloy elastomer composite membrane wall of the present invention forms a chamber which collects removed plaque temporarily and which also functions like the balloon used in the design of the prior art. In the present invention, upon the completion of the angioplasty procedure, a window in the cylindrical housing of the catheter can be closed off by a thin shutter door and the shape memory alloy elastomer composite membrane wall structure can be triggered to return to its original shape conforming to the cylindrical wall geometry of the housing structure. The mechanical stresses exerted during the transformation of the shape memory alloy structures result in pushing temporarily stored plaque into the catheter housing before the catheter is removed from the patient's body. Thus, the entire cutter housing structure is utilized as a final storage chamber and the shape memory alloy expandable membrane as a temporary storage structure for removing plaque that can eliminate the major disadvantages of the prior art including the Simpson Atherocath catheter previously described. The new catheter design of the present invention incorporates a shape memory alloy elastomer composite structure which serves the following functions: (1) In its original shape it serves as part of the housing structure which contains a cutter or other tissue removing device; (2) during the phase transformation of the shape memory alloy the membrane-like structure can expand and function in a manner similar to the balloon in the Simpson Atherocath catheter thereby effectively pressing the cutter against a portion of the artery blockage; (3) in the process of expanding, the shape memory alloy elastomer composite wall structure creates room for storing plaque removed by the cutter, the expansion of the shape memory alloy being made possible by the phase transformation of the shape memory alloy material and not by internal gas or liquid pressurization of a sealed membrane such as conventional balloon as accomplished in the prior art; and (4) at the completion of the catheterization and/or angioplasty procedure, the shape memory alloy elastomer composite wall structure can be returned to its original shrunken shape while simultaneously the temporarily stored plaque removed from the artery is transferred back to the cutter housing structure and the cut-out portion of the housing which exposes the plaque to the cutter may be closed off using a shutter mechanism which also uses shape memory alloy materials for purposes of activation.

OBJECTS OF THE INVENTION

It is therefore a principal object of the present invention to provide an improved catheter of the type used for cutting away or otherwise removing plaque or other blockage from an artery of the human body and which uses a shape memory alloy wall structure as a means for increasing the plaque storage capacity of the catheter.

It is an additional object of the present invention to provide an improved atherectomy catheter of the type having a housing and an open window adjacent which is provided a cutting device for removing plaque or other such blockage from the interior wall of an artery wherein the improvement comprises at least a portion of the housing having a shape memory alloy wire mesh structure which permits control, expansion and contraction of the wall of the housing to increase the plaque storage capacity of the catheter.

It is still an additional object of the present invention to provide an improved atherectomy catheter of the type having a housing and an opening therein and a cutting device and means for compressing the opening against blockage within an artery to permit the cutting device to remove such blockage therefrom and wherein the means for compressing the housing against the blockage comprises an expandable shape memory alloy structure which can be expanded and contracted by remote control without the use of fluid pressurization.

It is still an additional object of the present invention to provide an improved atherectomy catheter of the type having a housing and an opening therethrough and a cutter therewithin for removing plaque from the interior walls of an artery, the improvement comprising a shape memory alloy material shutter which may be remotely controlled for opening and closing the opening for increasing the storage capacity of the catheter housing thereby reducing the number of times it is necessary to remove the catheter from the patient during angioplasty procedures.

BRIEF DESCRIPTION OF THE DRAWINGS

The aforementioned objects and advantages of the present invention as well as additional objects and advantages thereof will be more fully understood hereinafter as a result of a detailed description of a preferred embodiment when taken in conjunction with the accompanying drawings in which.

DETAILED DESCRIPTION OF A PREFERRED EMBODIMENT

Figures 1, 10, 11, 12:
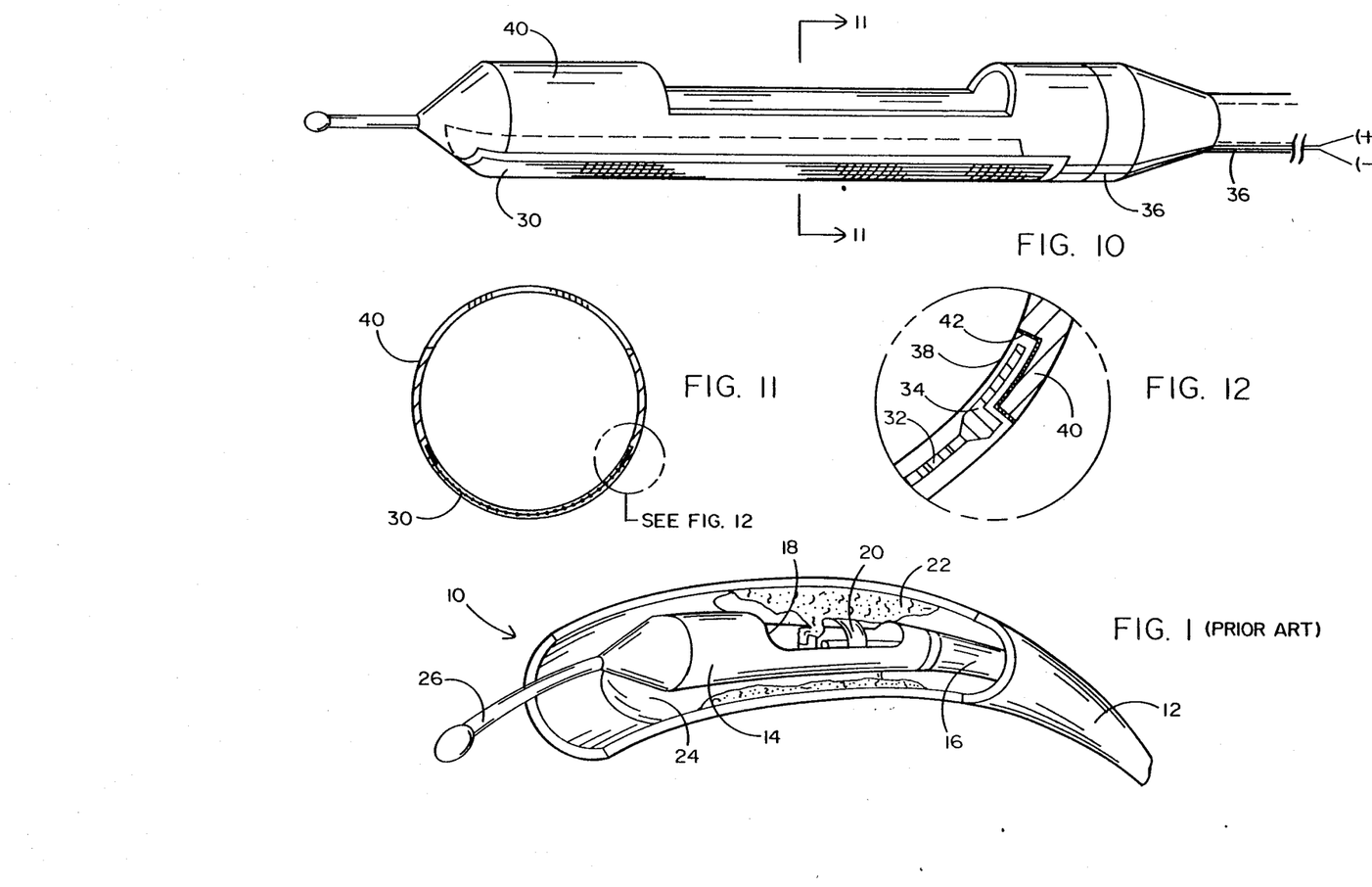
FIG. 1 is an isometric illustration of a prior art catheter of the type to which the improvement of the present invention is primarily directed.
FIG. 10 is an isometric illustration of the improved catheter of the present invention.
FIG. 11 is a cross-sectional view of the present invention taken along lines 11—11 of FIG. 10.
FIG. 12 is an enlarged view of that portion of FIG. 11 shown in the circle labelled "see FIG. 12"
Figure 2:
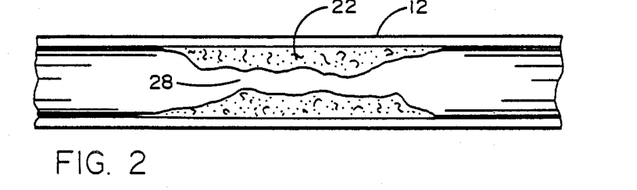
FIGS. 2-6 provide schematic illustrations of the sequence of steps used to remove plaque from an artery using the prior art catheter of FIG. 1.

Referring first to FIG. 1 it will be seen that a prior art atherectomy catheter device 10 which is designed to be inserted into an artery 12, comprises a housing 14 connected to a cutter torque cable 16. The housing provides a window 18 to permit access by a cutter 20 to a blockage or plaque 22 within the interior wall of the artery 12. The housing provides an exterior balloon 24 which is designed to compress against the interior wall of the artery 12 opposite the position of the cutter so that the cutter can come into contact with or remove the plaque or blockage 22 opposite the balloon 24. A spring tip 26 is also provided to facilitate easy insertion and removal of the catheter device 10 from the artery 12.

Figure 3:
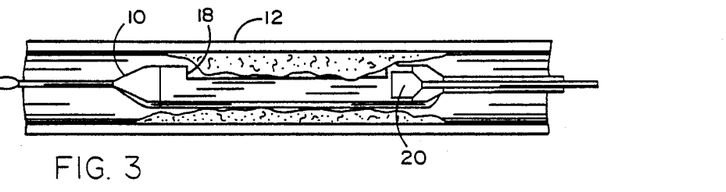
Figure 4:
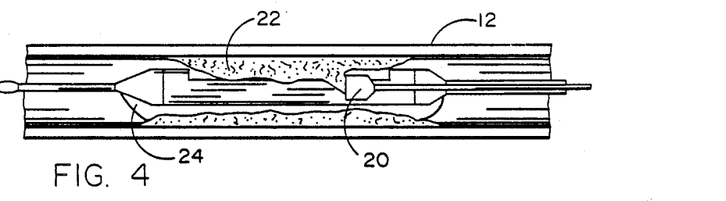
Figure 5:
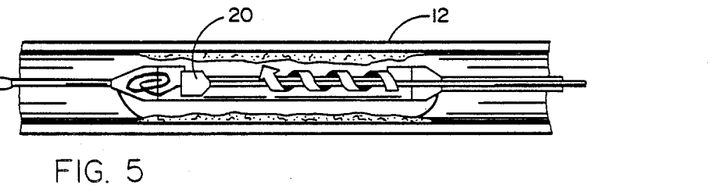
Figure 6:
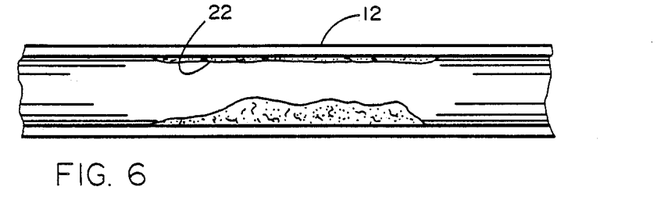

FIGS. 2-6 illustrate the manner in which the prior art catheter device 10 of FIG. 1 is designed to operate. More specifically, turning first to FIG. 2 it will be seen that the artery 12 includes an exemplary a blockage 22 through which there may be made a channel 28 which for example may be produced by a laser catheter in those cases where an artery is closed by complete blockages. Catheter 10 is then inserted into the artery 12 and clamped around a section of the blockage as shown in FIG. 3. The balloon 24, located beneath the catheter housing 14, is then inflated to apply pressure against the surface of the blockage to be sheared by the catheter device 10. A tiny rotating blade 20 is then activated as shown in FIG. 4 to slice off a piece of the plaque or blockage 22 and collect such sliced pieces of plaque inside the catheter housing as shown in FIG. 5. The catheter is then removed from the artery completing the procedure and leaving a relatively unblocked passage as shown in FIG. 6. Each time the interior of the housing of the catheter 10 is filled with cut plaque material, the catheter has to be removed from the artery 12 and emptied before it is reinserted into the artery.

Figure 7:
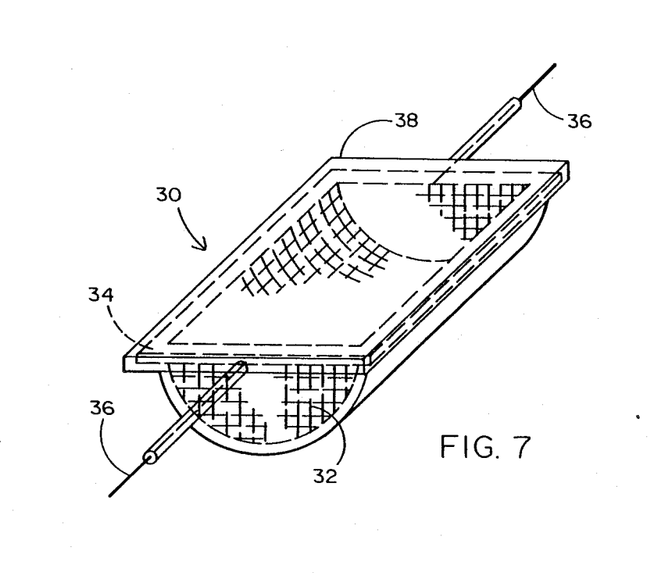
FIG. 7 is an isometric illustration of a wire mesh shape memory alloy structure comprising an improvement of the present invention which is adapted to modify the prior art catheter of FIG. 1.

In the present invention, the wall of the catheter housing 14 opposite the window 18 is replaced with an expandable basket integrated into the housing surface. Such an expandable basket 30 is shown in FIG. 7. Expandable basket 30 comprises a wire mesh structure 32 integrally supported by a metal frame 34 which is in turn connected to electrical conductors 36. Wire mesh 32 is composed of a shape memory alloy material in thin wire form that has been knitted, woven or braided into the basket configuration shown in FIG. 7. The wire ends at the edges of the basket structure are framed or crimped to a metal frame 34 which is selected to have a lower electrical resistance in comparison to the alloy making up the material of the mesh 32. The input-output insulated electrical conductive wires 36 are attached to the frame structure 34.

Figure 8:
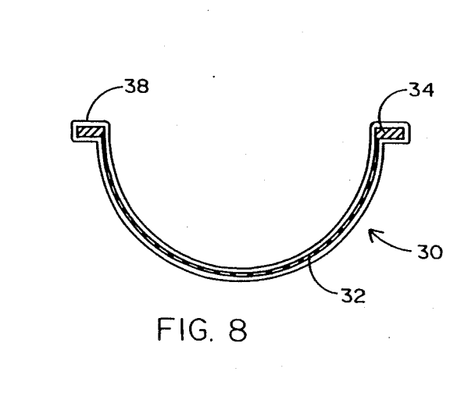
FIG. 8 is a cross-sectional illustration of the wire mesh structure of FIG. 7.

Because it is necessary to insulate the wire mesh thermally and electrically and to seal the pores for holding the removed plaque, the wire mesh 32 and metal frame 34 are enclosed in an elastomeric material 38 which may be either in a form of a thin film or a castable material which is used to laminate the wire mesh in the case of thin film or to impregnate in the case of castable. Elastomeric rubber materials which are either thermosetting or thermoplastic should preferably possess the following characteristics: They should be blood compatible and otherwise biocompatible for invivo application inside the blood vessel; they should have the proper viscoelastic property for stretching; proper range of electrical and thermo resistivity; and thermal stability over the temperature range required to activate the basket 30 and specifically, the shape memory alloy feature of the mesh 32 as will be hereinafter more fully explained. In addition, the elastomeric material should have adequate mechanical strength even after the reversible stretching process resulting from activation of the shape memory alloy. Based on these characteristics the elastomer 38 can be for example, one or more of the following materials: polyether urethane; polydimethyl siloxane; silicone rubber; polyvinyl chloride; polyurethane elastomer; polyethylene terephthalate and polypropylene. FIG. 8 provides a cross-sectional view of the expandable basket 30 of FIG. 7 illustrating the manner in which the elastomeric sheath 38 covers the entire structure thereof.

The most important characteristic of the expandable basket 30 is its ability to be expanded and contracted in size by remote control. This feature is provided by the use of a shape memory alloy which forms the material of wire mesh 32. As one example a shape memory alloy such as nickel-titanium alloy can be fabricated into wire form with a desirable cross-sectional geometry. Because the electrical resistivity of the nickel titanium alloy is approximately 70-100 microOhms centimeters under ambient conditions, which is of almost 50 times higher than the electrical resistivity of pure copper, the shape memory alloy wire can be heated up rapidly to reach the martensite to parent phase transformation temperature by simply passing electrical current through the wire 36 of FIG. 7. With a carefully controlled amount of electrical power, the surface temperature of the wire of mesh 32 will not rise significantly even when the core of the wire is heated well above the ambient temperature.

Figure 9:
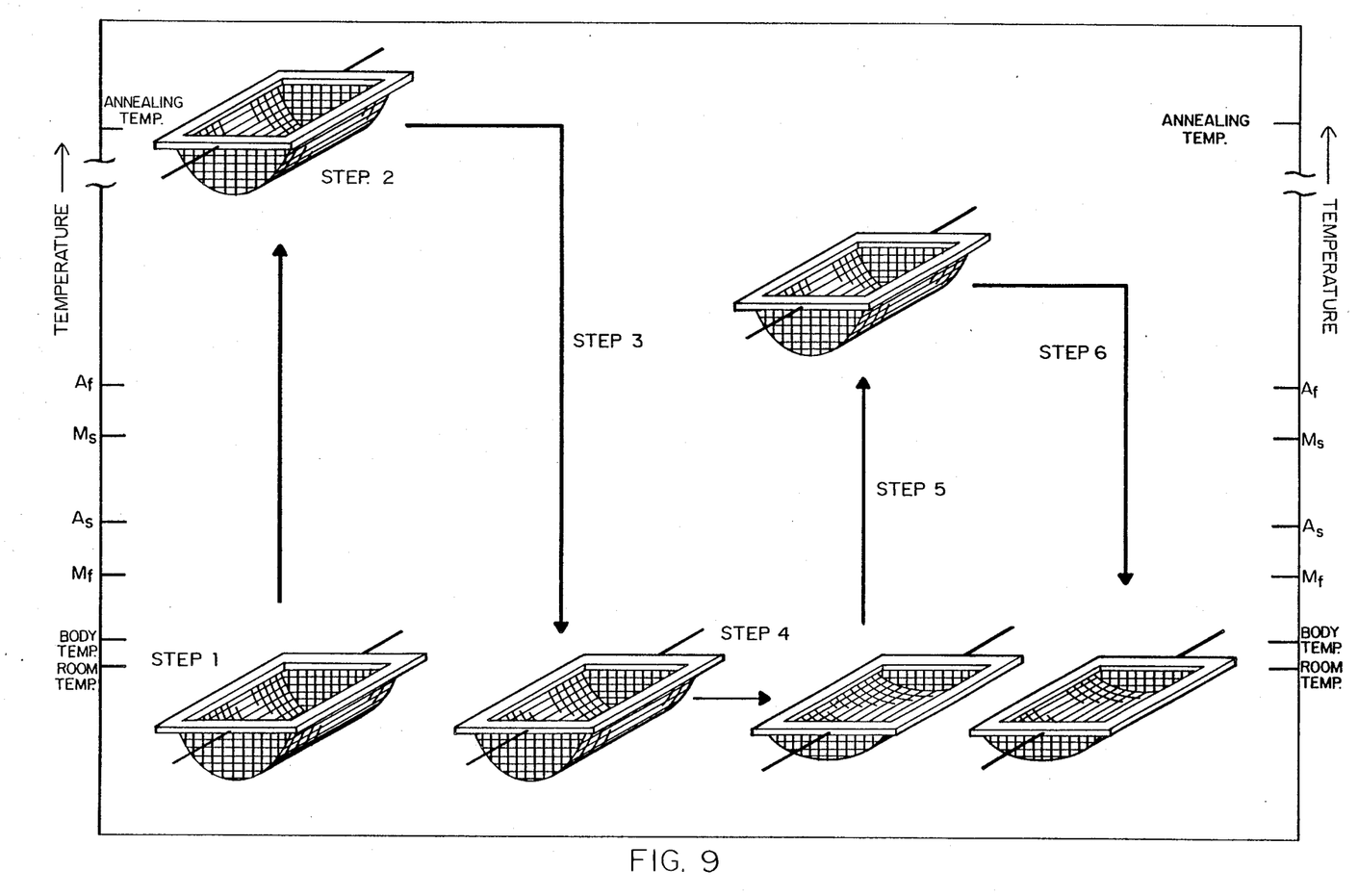
FIG. 9 is a graphical sequence illustration of the process used to manufacture the wire mesh structure of FIG. 7.
Figure 13:
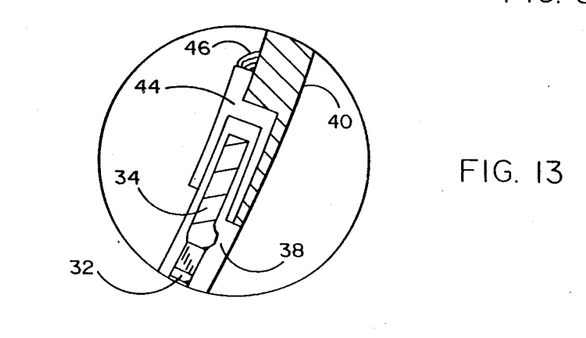
FIG. 13 is a view similar to that of FIG. 12 but illustrating an alternative interconnection for metal surfaces.

Because of the flexibility and pliability of the wire form, the shape memory alloy can be knitted, woven or braided into many different configurations depending upon the application. FIG. 9 illustrates sequentially, in a graphical format, the approach for fabricating and manipulating the wire mesh structure of the present invention. In step 1 of FIG. 9 the nickel-titanium shape memory alloy wire is knitted, woven or braided into a basket or pan-shape. The wire ends at the edges of the basket structure are framed or crimped to a metal structure as previously described and the electrically conductive wires are attached to the framed metallic structure. In step 2 the assembled structure is annealed at 650 degrees Centigrade plus or minus 300 degrees Centigrade to stabilize the shape memory alloy in its parent phase. In step 3 the structure is cooled below the temperature $M_f$ which is the temperature for the completion of the austenite to martensite transformation. The shape memory alloy can be formulated so that the temperature $M_f$ ranges from a few degrees to several hundred degrees Centigrade above normal body temperature of a human. In step 4 the framed basket structure is then passed with controlled stress level below the temperature $M_f$ to flatten the basket made from the shape memory alloy wire. In step 5 of FIG. 9, the flat wire mesh structure can be returned to the basket or pan-shape by passing an adequate amount of electrical current through the basket with a controlled voltage which raises the temperature in the core of the wire above the temperature $A_f$ which is the temperature for completion of the martensite to austenite transformation. In step 6, when the shape memory alloy is treated thermomechanically to possess "two-way" shape memory, the basket or pan-shape of the wire mesh structure can return to the flat configuration as the structure is cooled below the temperature $M_f$ by turning off or reducing the electrical power. The reversible phase transformation can be cycled many times if the composition of the shape memory alloy and special "two-way" memory thermomechanical treatment are carefully controlled. Also, under ideal conditions, the degree of shape changes between temperatures $M_s$ and $M_f$, where $M_s$ is the temperature for the start of the austenite to martensite transformation as well as between the temperatures $A_s$ and $A_f$, where $A_s$ is the temperature for the start of the martensite to austenite transformation, can be controlled to occur gradually by adjusting the input of the electrical power supply accordingly.

The attachment of a structure similar to the expandable basket 30 to the catheter housing 40 is shown in FIGS. 10-13. As shown in FIG. 10, the expandable basket 30 is integrated into the housing 40 by cutting out a large window in the lower part of the housing and substituting the basket 30 in place of the cut-out. The expandable basket 30 is now shaped to have a configuration matching perfectly the shape and dimensions of the cut-out portion of the catheter housing so that the cross-section thereof matches to form one continuous surface as shown in FIG. 11. In a preferred embodiment of the invention wherein the housing 40 of catheter is a nonmetallic material such as plastic, the interface between the expandable basket 30 and the housing 40 can be accomplished as shown in the enlarged view of FIG. 12. As shown in FIG. 12, the end of the metal frames 34 and the matching portion of the housing 40 are provided with complementary recesses which can be readily secured to one another by a bonding adhesive 42. It is, of course, important that the resulting joint and faying areas be made strong and smooth. The electrically conducting wires 36 leading in and out of the shape memory alloy structure, should be insulated by using biocompatible as well as blood compatible polymeric material and embedded in the housing and the remaining structure of the catheter. If metal is used as the housing material, then the periphery of the expandable basket 30 may be crimped by a metallic frame 44 shown in FIG. 13. Crimping frame 44 may be the same material as the metal frame 34 of the basket 30. The crimping frame 44 may be attached to the housing by using mechanical joining or various methods of welding and the like such as weld joint 46.

Figure 14:
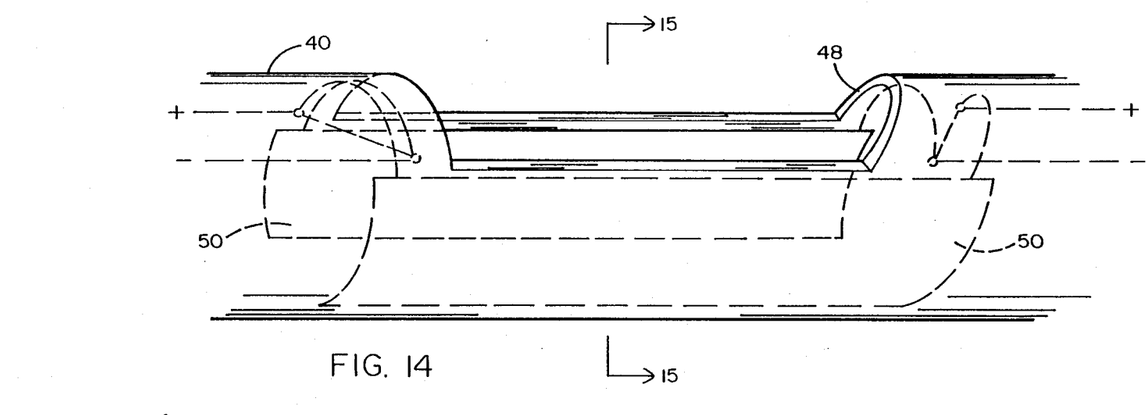
FIG. 14 is a enlarged partial view of a catheter of the present invention showing the use of shutters therein.
Figure 15:
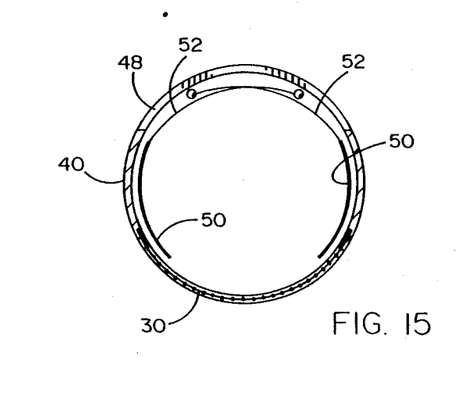
FIG. 15 is a cross-sectional view taken along lines 15—15 of FIG. 14.
Figure 16:
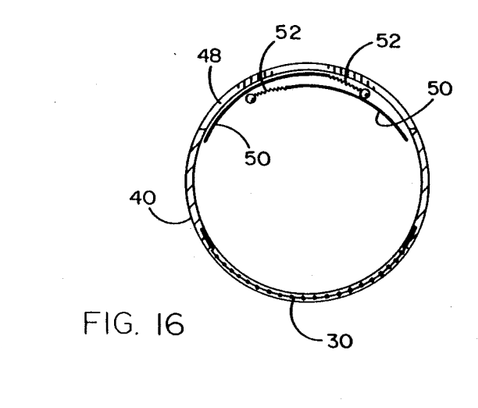
FIG. 16 is a view similar to that of FIG. 15 but showing the shutters in a closed position.
Figure 17:
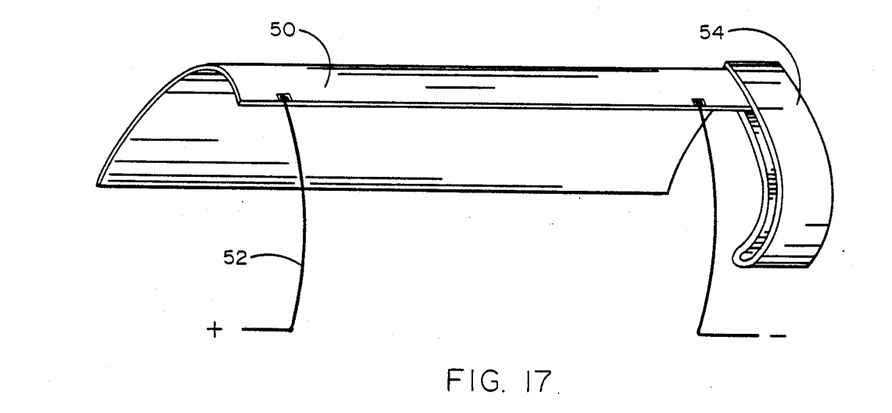
FIGS. 17 and 18 show the open and Closed position, respectively, of a shutter of the present invention.
Figure 18:
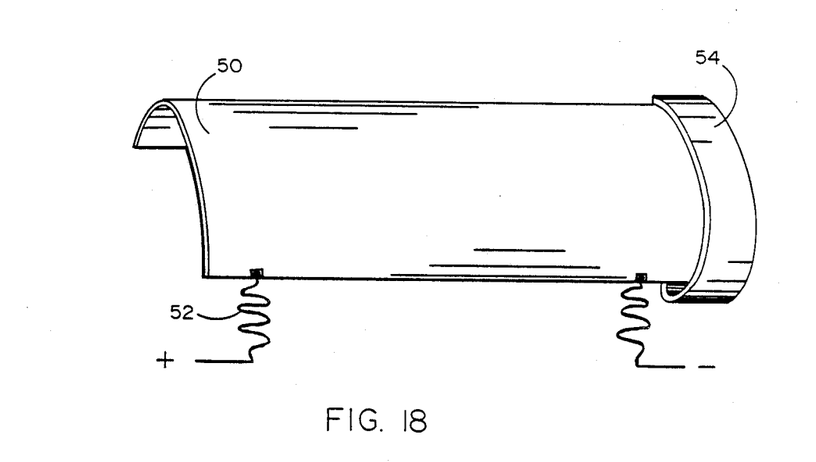

In order to utilize the entire housing structure of the catheter as a storage chamber during the final steps of the angioplasty procedure, using the present invention, the window through which the cutter gains access to the blockage should be closed so that the removed plaque cannot be flushed out from the housing structure to cause a potential problem. FIGS. 14–16 illustrate an embodiment of the present invention employing two overlapping leaflets or shutters 50 to open and close a window 48. The shutters 50 are fabricated using a thin sheet of blood/biocompatible plastic or metal. The shutters, in their overlapping configuration such as shown in FIG. 16, conform generally to the curvature and dimensions of window 48 in order to provide a secure closure of the catheter. In order to ease the sliding motion of the shutters 50 from open to close, a tracking guide 54 may be provided as seen in FIGS. 17 and 18 and may be attached to the interior side periphery of the window. The shutters can be actuated by using a shape memory alloy spring 52 controlled by the length of the shape memory alloy material as shown in FIGS. 15 and 16 and in FIGS. 17 and 18. The length of the shape memory alloy spring 52 can be readily changed as a result of a martensite to parent phase transformation triggered by the passage of electrical current in much the same way as the size of the expandable basket 30 of FIG. 10 is controlled.

Figure 19:
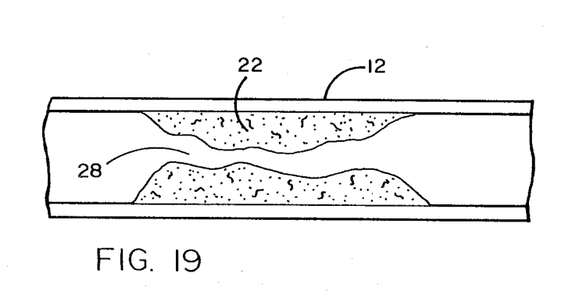
FIGS. 19-24 illustrate sequentially the manner in which an improved catheter of the present invention may be utilized.
Figure 20:
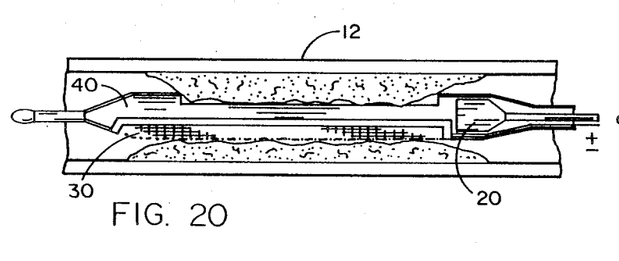
Figure 21:
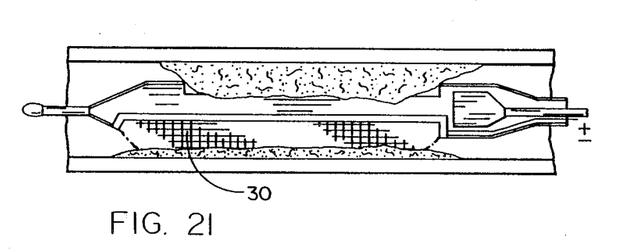
Figure 22:
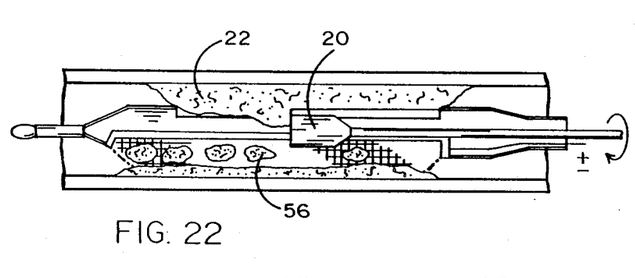
Figure 23:
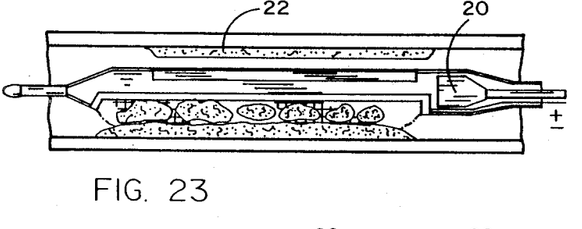
Figure 24:
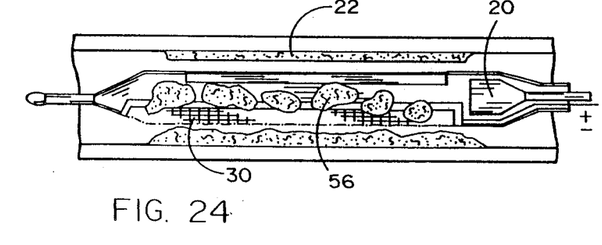

A detailed angioplasty procedure utilizing the catheter of the present invention is shown in sequence in FIGS. 19–24. Initially a laser catheter may be used to create a burn-through channel 28 as seen in FIG. 19, particularly in those cases where the artery is completely or severely blocked. The catheter of the present invention is then inserted into the artery 12 and clamped around a section of artery blockage 22. The location of the catheter can be carefully controlled by coordination with proper radiographic monitoring.

The shutter doors 50 are placed in the open position so that the edge of the housing window can be firmly placed against the blockage. A controlled level of electrical current at a predetermined voltage is supplied to the expandable basket 30 to trigger the martensite to parent phase transformation so that the expanded wire mesh 32 functions like a balloon by applying pressure against the blockage being sheared. By using a carefully calibrated relationship between electrical power versus degree of shape memory alloy structure shape change, the amount of structural expansion can be controlled to apply an adequate level of pressure on the blockage without damaging the artery.

A small rotating blade 20 may then be activated to slice off the plaque. However in this instance with the advantages derived from the present invention, instead of collecting the removed plaque only in the toe of the catheter housing, the plaque can be temporarily stored in the chamber created by the expanded basket 30 by dropping or squeezing through the cut-out of the housing to which the expandable basket 30 is attached.

After a sufficient amount of plaque is removed or when the expandable basket has been filled with the sheared plaque, the rotating blade 20 is withdrawn to the rear end of the catheter housing. A second separate electrical current is passed to the shape memory alloy wire 52 which controls the spring mechanism of the shutter doors 50 to trigger the martensite to parent phase transformation. The shutter door is now in the closed position to seal off the housing window of the catheter. The electric power to the expandable basket 30 is then cut off or substantially reduced so that the temperature of the shape memory alloy mesh 32 within the expandable basket structure drops below the temperature $M_f$. The expandable basket then returns to its shape conforming to the housing cut-out and the temporarily stored plaque is pushed back into the sealed catheter housing due to sufficient force exerted during the phase transformation. The catheter is removed from the patient's body, completing the procedure.

It will now be understood that what has been disclosed herein comprises an improved catheter which utilizes a shape memory alloy structure as an integral part of the wall of the housing structure of a Simpson Atherocath catheter or other similar types of catheters and which may also use a shape memory alloy material as a remotely controlled actuator for a shutter door to open and close an opening into the housing of such a catheter. The integral wall structure portion of the invention employs a combination of shape memory alloy wire mesh in a basket configuration covered in an elastomer permitting it to expand as desired like a balloon, but without utilizing gas or liquid pressurization for the purpose of structural inflation. As a result, the present invention provides a remotely controllable expandable chamber which can collect removed plaque temporarily and which also functions like the balloon used in the design of the prior art to compress the catheter housing against the interior wall of an artery. In addition, upon completion of an angioplasty procedure utilizing the present invention, a window in the housing of the catheter can be closed off by a thin shutter door thereby securing the pieces of removed plaque within the shutter housing and in addition the shape memory alloy elastomer composite membrane wall structure of the invention can be triggered to return to its original shape conforming to the cylindrical wall geometry of the housing structure for easy and safe removal of the catheter and the stored plaque contained within the housing.

Those having skill in the art to which the present invention pertains will now, as a result of the applicant's teaching herein, perceive various modifications and additions which may be made to the invention. By way of example, other materials including other shape memory alloy materials and conventional materials may be utilized as substitutes for the materials disclosed herein. In addition, shapes other than those specifically disclosed herein may also be substituted herein without deviating from the purposes and performance of the invention as disclosed. Accordingly, all such modifications and additions are deemed to be within the scope of the invention which is to be limited only by the claims appended hereto.

I claim:

1. An improved catheter, the catheter of the type used in a human artery for removing an arterial blockage therein using a mechanical or electromechanical or electro-optical plaque removal device such as a rotating blade within a cylindrical housing adjacent an opening through the radial wall of the housing, the rotating blade cutting pieces of plaque which are received and temporarily stored in the housing; the improvement comprising:

in said housing an integral, expandable wall portion positioned substantially opposite to said opening and being formed of a mesh of shape memory alloy wire responsive to changes in temperature for selective changes in dimension;

means for remotely controlling the temperature of said mesh wire for selectively expanding and contracting said wall portion while said catheter is in said artery.

2. The improvement recited in claim 1 wherein said wire mesh is encased within an elastomeric material.

3. The improvement recited in claim 1 wherein said expandable wall portion further comprises a metallic frame as well as an elastomeric sheath providing an interface with said catheter housing.

4. The improvement recited in claim 1 wherein said temperature controlling means comprises a source of electrical current and means for directing said electrical current through said wire mesh.

5. The improvement recited in claim 1 further comprising at least one remotely controlled shutter for selectively opening and closing said catheter opening.

6. The improvement recited in claim 5 wherein said remotely controlled shutter comprises a spring activation member made of a shape memory alloy responsive to changes in temperature for moving said shutter into and out of said opening.

7. The improvement recited in claim 6 further comprising an electrical current source and means connecting said current source to said spring activation member for passing selected magnitudes of current through said member for varying the temperature thereof for opening and closing said opening.

8. An improved catheter, the catheter of the type used in a human artery for removing an arterial blockage therein using a mechanical plaque removal device such as a rotating blade within a cylindrical housing adjacent an opening through the radial wall of the housing; the improvement comprising:

a door cooperating with said opening for selectively opening and closing said opening while said catheter is in said artery; and means for actuating said door and having a shape memory alloy material responsive to electrical current-induced temperature changes.

9. The improvement recited in claim 8 wherein said actuating means comprises a length of shape memory alloy wire which responds to temperature change by shortening its length and increasing its length to alter the position of said door.

10. The improvement recited in claim 8 further comprising:

a shape memory alloy structure affixed to said housing substantially opposite of said opening for radial expansion in response to temperature change while within said artery whereby to force said opening against said blockage.

11. A catheter comprising a cylindrical housing for insertion into an artery, at least a portion of said housing being made of a shape memory alloy for selective expansion in response to temperature changes whereby to cause said housing to forcefully engage the interior of said artery.

12. The catheter recited in claim 11 further comprising:

means for applying an electrical current to said shape memory alloy for selectively expanding and contracting said housing portion.

13. The catheter recited in claim 11 wherein said housing has a radial opening; said housing comprising remotely controlled means for opening and closing said opening.

14. The catheter recited in claim 13 wherein said remotely controlled means comprises a door, a shape memory alloy actuator for opening and closing said door and a source of electrical current for selectively altering the temperature of said door actuator.

* * * * *